United States Patent
Anglada et al.

(10) Patent No.: US 9,463,108 B2
(45) Date of Patent: Oct. 11, 2016

(54) ORTHOSIS FOR TREATING MUSCLE DISORDERS IN THE ELBOW

(75) Inventors: Gerard Anglada, Saint Etienne (FR); Frederic Girard, Paris (FR)

(73) Assignee: GIBAUD, Saint Etienne (FR)

( * ) Notice: Subject to any disclaimer, the term of this patent is extended or adjusted under 35 U.S.C. 154(b) by 459 days.

(21) Appl. No.: 14/000,082

(22) PCT Filed: Feb. 3, 2012

(86) PCT No.: PCT/FR2012/050240
§ 371 (c)(1),
(2), (4) Date: Oct. 1, 2013

(87) PCT Pub. No.: WO2012/114012
PCT Pub. Date: Aug. 30, 2012

(65) Prior Publication Data
US 2014/0024987 A1    Jan. 23, 2014

(30) Foreign Application Priority Data

Feb. 21, 2011    (FR) ..................................... 11 51405

(51) Int. Cl.
A61F 5/01    (2006.01)
(52) U.S. Cl.
CPC .............. *A61F 5/013* (2013.01); *A61F 5/0118* (2013.01)
(58) Field of Classification Search
CPC combination set(s) only.
See application file for complete search history.

(56) References Cited

U.S. PATENT DOCUMENTS

| | | | | |
|---|---|---|---|---|
| 4,862,877 A | * | 9/1989 | Barber | A61F 5/05866 602/22 |
| 5,358,471 A | * | 10/1994 | Klotz | A61F 5/013 602/16 |
| 5,672,150 A | * | 9/1997 | Cox | A61F 5/0118 128/879 |
| 5,759,165 A | * | 6/1998 | Malewicz | A61F 5/0125 602/16 |
| 5,836,902 A | | 11/1998 | Gray | |
| 2004/0024339 A1 | | 2/2004 | De Lint | |
| 2006/0089583 A1 | | 4/2006 | Reinhardt | |
| 2008/0034459 A1 | * | 2/2008 | Nordt, III | A61F 5/0118 2/16 |

OTHER PUBLICATIONS

International Search Report issued in PCT/FR2012/050240, dated Jun. 5, 2012.

* cited by examiner

*Primary Examiner* — Ophelia A Hawthorne
(74) *Attorney, Agent, or Firm* — Workman Nydegger

(57) ABSTRACT

An orthosis for treating muscle disorders of the elbow has a body made in one piece from a semi-rigid material. The body includes a distal portion, a proximal portion, and a back joining strap. In the unstressed state, the relative position of the distal and proximal portions maintains the wrist in an extended state. The joining strap is deformable such that when pressure is exerted downward on the palm support, the joining strap is deformed to enable the pivotal movement of the distal portion with respect to the proximal portion about a transverse articulation axis parallel to the flexion-extension axis of the wrist. When pressure is released, the body returns to the unstressed state due to resilience. The distal portion is arranged to pivot with respect to the proximal portion about the articulation axis while assisting the extensor muscles of the wrist.

10 Claims, 4 Drawing Sheets

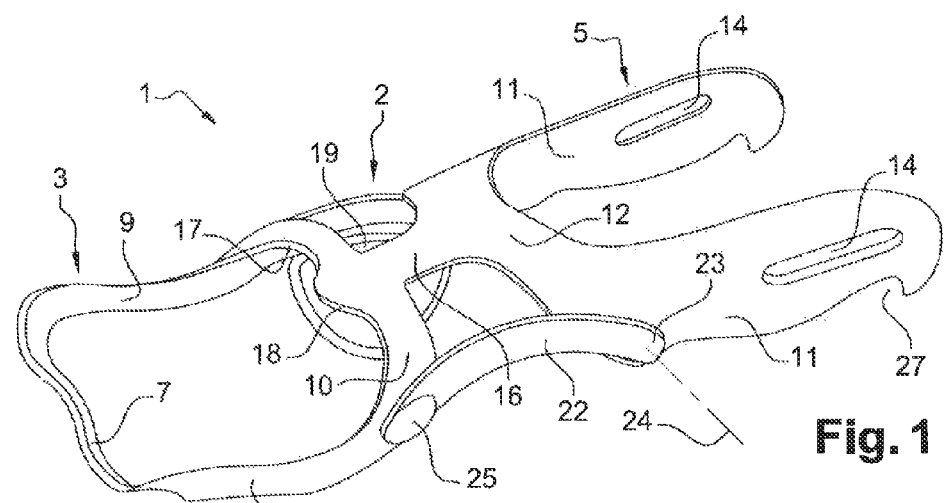
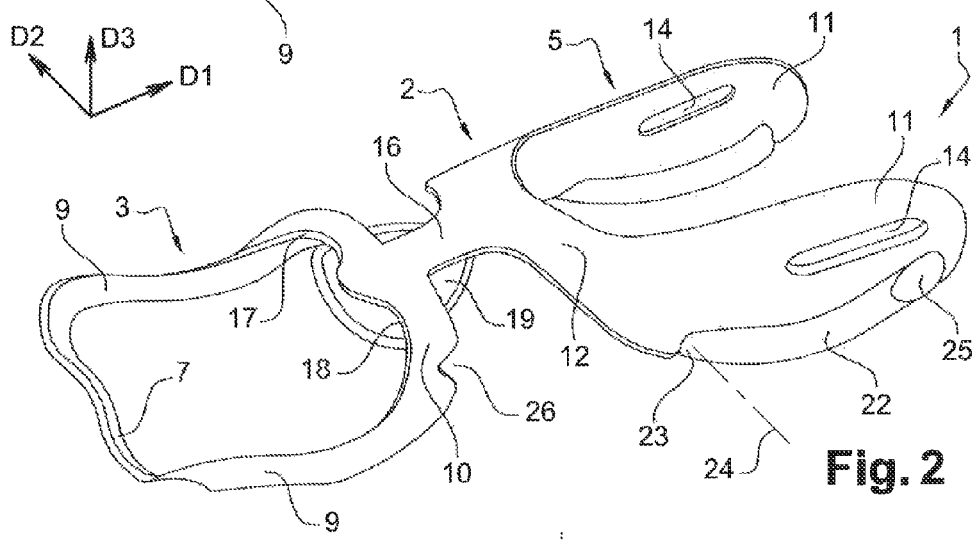
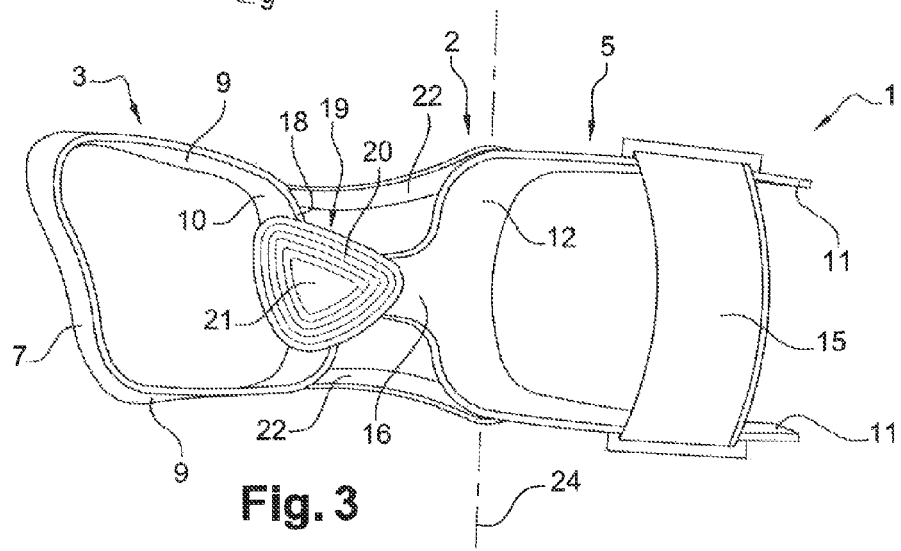

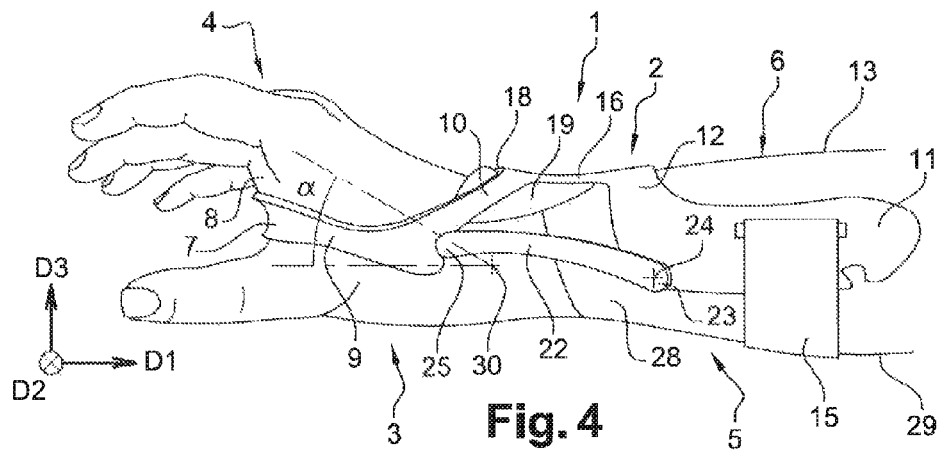
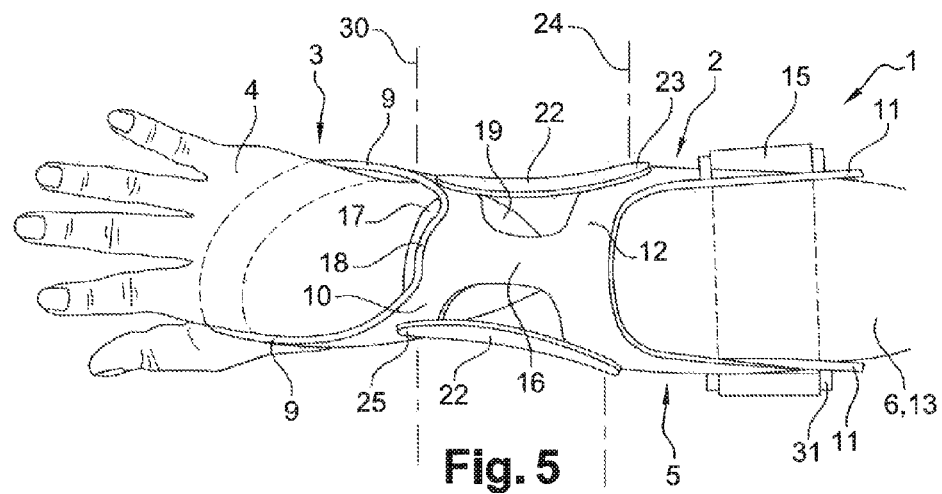
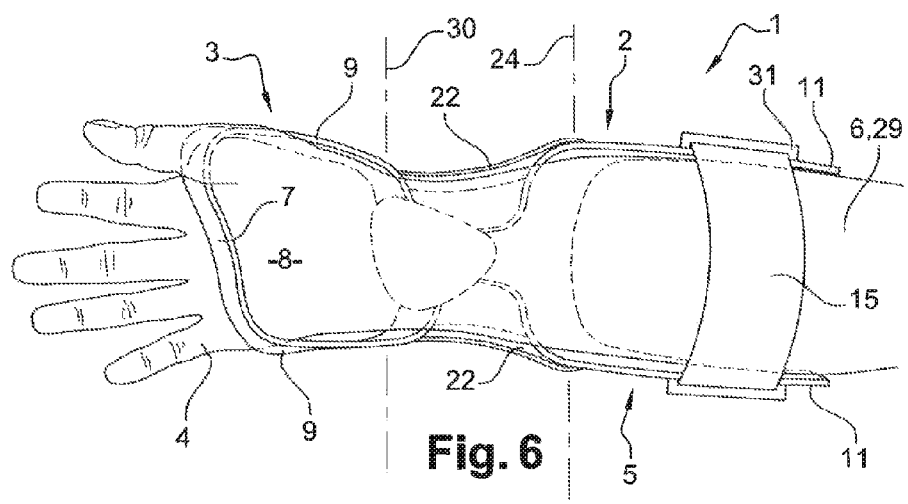

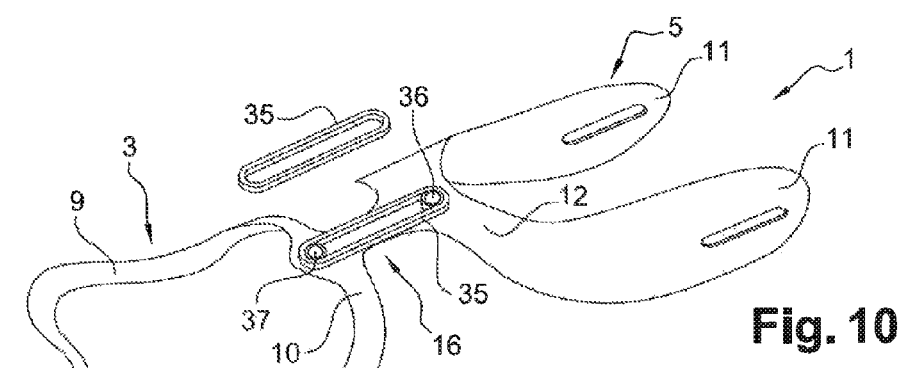
Fig. 10
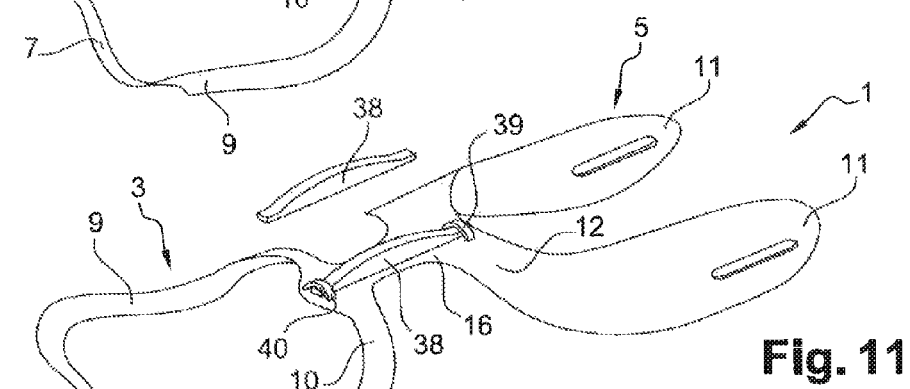
Fig. 11
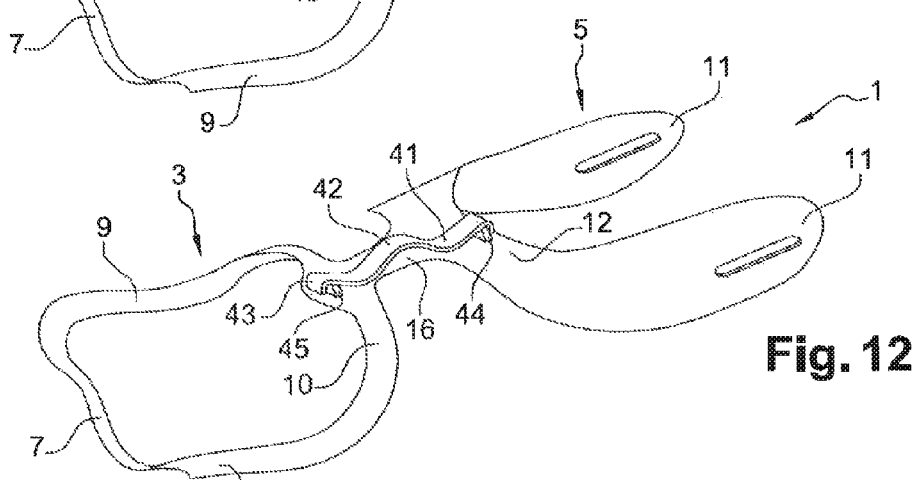
Fig. 12
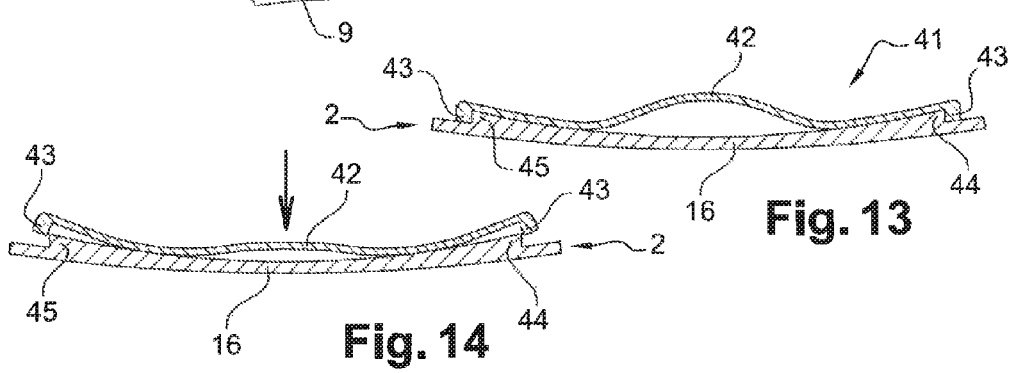
Fig. 13
Fig. 14

ORTHOSIS FOR TREATING MUSCLE DISORDERS IN THE ELBOW

BACKGROUND

The present invention concerns an orthosis for elbow muscle disorders which is capable of assisting the extensor muscles of the wrist.

One of the muscle disorders more specifically concerned by the present invention is epicondylitis. This is tendinitis having the signs of elbow pain which is often the result of too much demand placed on the muscles of the forearm. This disorder may particularly occur subsequent to repetitive movements which are ill-executed or particularly hard to perform by the hand and/or wrist whether at the workplace (carpenters, builders, operators of pneumatic drills, etc.) or when practising a sport (tennis, golf, etc.) or leisure activity (e.g. gardening). Epicondylitis may therefore occur when too much stress is placed on the tendon of the extensor muscles; pain is especially felt in the outer part of the forearm, in the region of the epicondyle which is a small bony projection on the outer surface of the humerus.

This disorder causes pain which may last a few weeks and even longer, and if not properly treated may degenerate into chronic pain and cause irreversible lesions.

At the start of the attack, it is preferable to give the elbow at at least partial rest by avoiding or at least controlling those movements which caused the lesion. Later, during the re-adaptation phase, it may be possible gradually to resume movement preferably wearing a device tightly supporting the forearm which allows stresses on the tendon to be limited by locally compressing the muscle.

SUMMARY

The present invention sets out to provide an orthosis which can be used during an acute phase of epicondylitis, in particular, which can relieve and treat the user, whilst enabling the user when needed to perform a certain number of movements that are non-harmful for the muscle disorders concerned.

The invention therefore concerns an orthosis for treating muscle disorders of the elbow, such as epicondylitis, capable of assisting the extensor muscles of the wrist. According to the invention, the orthosis comprises a body made in a single piece in semi-rigid material, the body comprising:
  a distal portion intended to be positioned at the level of the hand, comprising a substantially transverse palm support for the palm of the hand, extended in the proximal direction by two substantially longitudinal lateral branches which are joined at their proximal end by a substantially transverse distal bridge intended to cover the posterior side of the wrist;
  a proximal portion intended to be positioned at the level of the forearm, comprising two substantially longitudinal lateral wings intended to bear upon either side of the forearm and which are joined at their distal end by a substantially transverse proximal bridge intended to cover the posterior side of the forearm;
  a back joining strap extending substantially longitudinally and connecting the distal and proximal bridges;
  a strap being associated with each of the lateral wings of the proximal portion to hold the lateral wings tight against each other and passing underneath the anterior side of the forearm, the body of the orthosis having a geometry such that the relative position of the distal and proximal portions, in the non-stressed state, corresponds to supported extension of the wrist when the orthosis is worn, and the back joining strap being elastically deformable so that:
    when pressure is applied to the palm support opposite the joining strap, the joining strap becomes deformed so as to allow pivoting of the distal portion relative to the proximal portion about an articulation axis which is substantially transverse and parallel to the flexion-extension axis of the wrist when the orthosis is worn;
    and when said pressure is released, the body returns to the non-stressed state via elasticity by pivoting of the distal portion relative to the proximal portion about the said articulation axis.

In practice, first, the pronosupination movement, which generates pain in the event of disorders concerned by the invention, is prevented or at least restricted by means of the presence of the lateral wings and branches on the body of the orthosis.

Also, in rest position—i.e. in the non-stressed state of the body of the orthosis—the wrist is supported in extension, which provides relief for the extensor muscles. For example, the wrist is held at an extension in the order of 20 to 40°, typically in the order of 30°.

Starting from the rest position, the user is able to bend the wrist against resistance to deformation of the body of the orthosis. This flexion therefore involves some effort but it is limited due to the elastically deformable nature of the joining strap. In addition, in cases of the disorders concerned by the invention, the flexion movement of the wrist is in general neither harmful nor painful.

Once the wrist is flexed, in particular for return to the rest position, the extension of the wrist is accompanied by the elastic return effect of the body of the orthosis. As a result there is no or only little demand placed on the extensor muscles.

It is to be noted that with the orthosis of the invention, it is essentially, even solely, the joining strap which becomes deformed and not the lateral branches or wings.

Another advantage of the invention lies in the <<dorso-palmar>> geometry of the orthosis: the fact that the semi-rigid portions of the orthosis are respectively positioned on the forearm and underneath the hand makes it possible to obtain a lever arm effect which guarantees the orthosis is very well maintained in position without excessive compression. With this provision it is possible to distribute stress over a wider surface area of the user's hand and forearm without substantial tightening of the orthosis being necessary. In addition, advantageously, provision can be made so that the strap only passes underneath the anterior side of the forearm i.e. not on the posterior side of the forearm.

By <<semi-rigid>> is meant that the body of the orthosis has both sufficient rigidity to adopt a given geometry in the non-stressed state, and providing the desired support in extension, and a certain capacity for elastic deformation to allow flexion.

The invention therefore provides a dynamic orthosis which, in practically free manner, allows the performing of some non-deleterious movements. One first corresponding advantage is that the wearing of the orthosis is less restrictive for daily life which means that a user will be more inclined to wear this orthosis. This can avoid the inflammation from becoming chronic by limiting the demand placed on the epicondyle muscles. Another advantage is the prevention of prolonged immobilisation which, in some cases, could cause serious stiffening of the joint, which is sometimes irreversible. In addition the orthosis also permits the performing of harmful or painful movements, but with accompaniment, which cancels their deleterious effect and offers the user relative freedom for everyday living.

According to one possible embodiment, the orthosis is free of any member that comes to bear upon the dorsal side of the hand such as a strap or equivalent. The <<dorso-palmar>> geometry of the orthosis is sufficient to ensure the orthosis is very well maintained in position without requiring additional support on the dorsal side of the hand, which could generate problems of excessive tightening, could be detrimental to wearer comfort and/or hinder wrist movements.

The orthosis may also comprise rigidifying means designed to be able to prevent deformation of the body of the orthosis when pressure is applied on the palm support opposite the joining strap. The orthosis therefore allows immobilisation of the wrist in extension and prevents flexion of the wrist. This can be of use particularly during a serious phase of the disorders concerned by the invention.

According to one possible embodiment, the rigidifying means comprise a rigid part which can be removably attached onto the joining strap so as to prevent elastic deformation of this joining strap.

As a variant or in addition, the rigidifying means may comprise at least one rigid member mounted on the proximal portion, and respectively on the distal portion, of the body of the orthosis so that it pivots about a substantially transverse axis between an active position in which the member is fastened onto the distal portion, respectively onto the proximal portion, by retaining means to prevent deformation of the body of the orthosis, and an inactive position in which the member allows deformation of the body of the orthosis. These rigidifying means therefore form a captive fastening system.

Said member may comprise a lateral tab having a first end which is mounted on a lateral wing of the proximal portion, respectively a lateral branch of the distal portion of the body of the orthosis, and a second end which is provided with removable retaining means on said lateral branch and on lateral side wing, in active or inactive position. In substance, if the first end of the tab is pivot mounted on the proximal portion, the second end of the tab can be held on the lateral branch in active position and on the lateral wing in inactive position.

BRIEF DESCRIPTION OF THE DRAWINGS

A description will now be given via non-limiting examples of several possible embodiments of the invention with reference to the appended figures.

FIG. 1 is a perspective view of an orthosis according to one embodiment of the invention, with rigidifying means in active position;

FIG. 2 is a similar view to FIG. 1, the rigidifying means being in inactive position;

FIG. 3 is an underside view of the orthosis in FIG. 1;

FIGS. 4 to 6 illustrate an orthosis worn by a user, from a lateral view, posterior view and anterior view respectively;

FIGS. 10 to 12 are perspective views of an orthosis according to the invention, equipped with rigidifying means according to three different embodiments;

FIGS. 13 and 14 are partial views of the orthosis in FIG. 12 according to a longitudinal cross-section, showing the rigidifying means in mounted position and when being separated from the body of the orthosis.

DETAILED DESCRIPTION OF VARIOUS EMBODIMENTS

Figure 7:
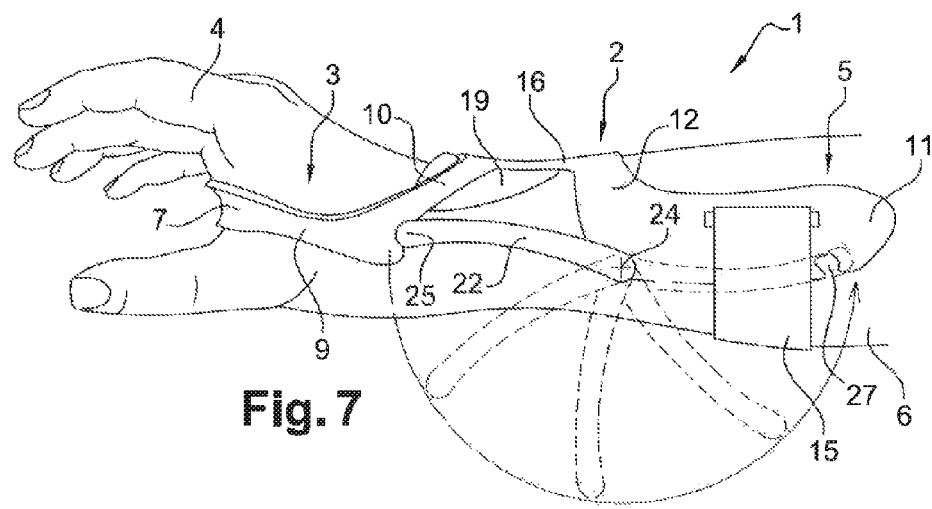
FIG. 7 illustrates the pivoting of the rigidifying means of the orthosis in FIG. 1, from the active position to the inactive position.

As illustrated in the figures, an orthosis 1 according to the invention comprises a body 2 made in a single piece in semi-rigid material e.g. polyamide. Advantageously, provision can be made for the body 2 of the orthosis 1 to be transparent or translucent so as to obtain a discreet item to wear. This adds to the non-cumbersome appearance and lightweight of the orthosis 1 which can be worn under clothing.

The body 2 comprises a distal portion 3 intended to be positioned at the level of the hand 4 of a user and a proximal portion 5 intended to be positioned at the level of the forearm 6.

The longitudinal direction D1 is defined as the general direction in which the forearm extends (when the orthosis 1 is worn), the transverse direction D2 is defined as the direction of articulation of the wrist in flexion/extension, and the vertical direction D3 as the direction of articulation of the wrist in adduction/abduction. The terms <<proximal>> and <<distal>> are used with reference to direction D1 and the term <<lateral>> is used with reference to direction D2.

The distal portion 3 comprises a substantially transverse palm support 7 for the palm 8 of the hand 4, extended in the proximal direction by two substantially longitudinal lateral branches 9 which are joined at their proximal end by a substantially transverse distal bridge 10 which is intended to cover the posterior side of the wrist.

The proximal portion 5 comprises two substantially longitudinal lateral wings 11 intended to bear on either side of the forearm 6 and which are joined at their distal end by a substantially transverse proximal bridge 12 intended to cover the posterior side 13 of the forearm 6. Each wing 11 may comprise an orifice 14 for the passing of a strap 15, the orifices 14 preferably extending substantially longitudinally. The strap 15 may pass through loops 31 each positioned on a lateral wing 11 (see in particular FIG. 6). The positioning of these loops 31 allows sliding of the strap 15 without pinching the skin.

In addition, the body 2 of the orthosis 1 comprises a back joining strap 16 extending substantially longitudinally and connecting the distal bridge 10 and the proximal bridge 12. The distal portion 3, the proximal portion 5 and the back joining strap 16 are made in a single piece.

Provision can be made so that the distal bridge 10 comprises a notch 17 arranged on its distal edge 18, the said notch 17 being located in the region of the ulnar styloid when the orthosis 1 is worn. With this provision it is possible to prevent pain related to bearing of the orthosis 1 on the ulnar styloid.

The orthosis 1 may further comprise a cushion 19 fixed underneath the dorsal—or posterior—part of the body 2 of the orthosis 1, underneath at least one part of the distal bridge 10 and of the joining strap 16, so that the cushion 19 is able to be inserted between the user's wrist and the body 2 of the orthosis 1. The cushion 19 is therefore able in particular to bear upon the ulnar styloid which allows solving of any positioning problems of the notch 17 in relation to the morphology of the user, although the orthosis 1 can exist in several sizes. The cushion 19 therefore allows the preventing of any painful bearing on the ulnar styloid.

More specifically, the cushion 19 can be attached to the body 2 of the orthosis 1 so as to bear upon the dorsal region of the radiocarpal. In addition, the cushion 19 allows the bearing of the body 2 of the orthosis 1 to be moved onto a surface—which furthermore is advantageously relatively flexible—rather than onto an edge—namely the distal edge 18 of the distal bridge 10. It therefore has the effect of distributing pressure.

As illustrated in FIG. 3, the cushion 19 may comprise at least one raised part 20 extending substantially crosswise and facing the hand when the orthosis 1 is worn 1. This notably allows the preventing of forward sliding of the orthosis 1. The cushion 19 is of globally oval or triangular shape for example comprising several raised portions 20 on its side 21 facing the hand 4 which follow the contour of the cushion 19 and are arranged in concentric fashion.

The cushion 19 is preferably in material having non-skid properties such as silicon or SEBS (styrene ethylbutylene styrene). This allows reinforcement of the adhesion of the cushion 19 as a variant to or in addition to the raised portion(s) 20.

In one embodiment illustrated in FIGS. 1 to 9, the orthosis 1 also comprises rigidifying means which comprise two rigid lateral tabs 22.

Each lateral tab 22 has a first end 23 which is mounted on the distal part of a lateral wing 11 of the proximal portion 5 so as to pivot about a substantially transverse axis 24. In addition, each lateral tab 22 has a second end 25 which is provided with removable retaining means on the proximal part of the corresponding lateral branch 9.

A tab 22 is therefore able to pivot about the axis 24, between an active position in which the second end 25 of the tab 22 is fastened onto the lateral branch 9 (FIG. 1) and an inactive position in which the second end 25 of the tab 22 is fastened onto the lateral wing 11 (FIG. 2).

The retaining means arranged on the tab 22 may comprise a projection able to engage either in a notch 26 (or orifice) arranged on the lateral branch 9 in active position, or in a notch 27 (or orifice) arranged on the lateral wing 11 in inactive position. The orthosis may therefore be used alone but its therapeutic action can be completed with the combined use of an elbow support.

As illustrated in FIG. 4, the orthosis 1 may further comprise an elbow support 28 in the form of a fabric sleeve. In practice, when the orthosis 1 is worn, the body 2 of the orthosis 1 is positioned over the elbow support 26. In other words, first the elbow support 28 is fitted to surround the elbow and extend either side thereof which allows limiting of elbow movements. Advantageously, the distal edge of the elbow support 28 is positioned in the vicinity of the wrist. In this manner, at least the proximal portion 5 of the body 2 and the strap 15 come to be placed on the elbow support 28.

In practice, the orthosis 1 is fitted as follows.

As a preliminary the user may put the elbow support 28 in place. The user's hand 4 is then placed in the distal portion 3, the palm against the palm support 7 and the thumb underneath this palm support 7. At this step, the hand 4 may be aligned with the forearm 6 i.e. neither in flexion nor in extension.

The user then tightens the strap 15. This has the effect firstly of placing the proximal portion 5 in position at the forearm 6 i.e. folding back the proximal portion 5 against the forearm 6, of placing the joining strap 16 flat against the wrist and of tightening the lateral wings 11 of the proximal portion 5 against each other, these wings possibly having some elasticity. The forearm 6 is therefore gripped by these two wings 11 and by the strap 15. It is a lower strap i.e. which passes solely against the anterior side 29 of the forearm 6. The body 2 of the orthosis 1 is thereby stabilised on the forearm 6 irrespective of its circumference and limits pronosupination movements which generate pain in epicondylitis.

The tightening of the strap 15 also has the effect of lifting the palm 8 of the hand 4 by causing the wrist to pivot around its flexion-extension axis 30 so as to maintain the wrist in extension. Since the distance—along D1—between the axis 30 and the distal end of the distal portion 3 is shorter than the distance—along D1—between the axis 30 and the strap 15, this operation is performed without excess tensioning.

The tabs 22 if not already in active position, can be placed in the active position to make the body 2 of the orthosis 1 substantially non-deformable and therefore prohibit flexion of the wrist. This strict immobilisation of the wrist can be imposed in some cases, for example, depending on the seriousness of the disorders, especially at the outset.

FIGS. 4 to 6 show the orthosis 1 being worn by a user in rest position i.e. in the non-stressed state of the body 2. The relative position of the distal 3 and proximal 5 portions is then such that the wrist is held in extension at an angle α in the order of 30°. On this account, the contraction of the extensor muscles (epicondyle muscles) and of their inflamed tendons is no longer needed to support the wrist.

Figure 8:
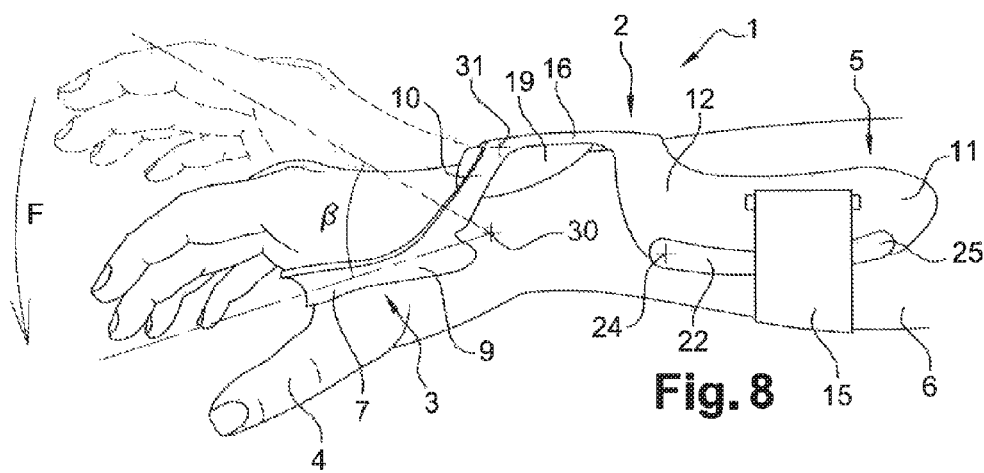
FIG. 8 illustrates the flexion movement of the wrist allowed by the orthosis.
Figure 9:
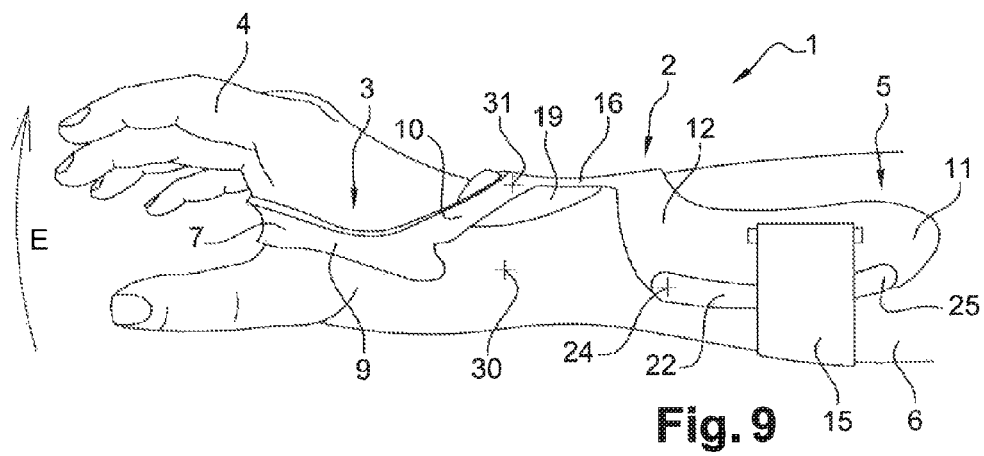
FIG. 9 illustrates the extension movement of the wrist assisted by the orthosis.

Reference is now made to FIGS. 7 to 9 which correspond to a use of the deformability properties of the body 2.

As illustrated in FIG. 7, starting from the position illustrated in FIG. 4, the tabs 22 if initially in active position are moved by pivoting about the axis 24 so that they are folded back and each fastened onto the corresponding lateral branch 11 in inactive position. The tabs 22 are held between the inner and outer parts of the strap 15. Flexion of the body 2 of the orthosis 1 is then possible.

Despite the semi-rigid nature of the constituent material of the body 2, on account of the reduced width and thickness of the joining strap 16, this strap can be elastically deformed when pressure is applied to the palm support 7 opposite the joining strap 16—i.e. downwardly in the illustration in FIG. 8. This deformation of the joining strap 16 allows pivoting of the distal portion 3 relative to the proximal portion 5 of the body about an articulation axis 31 which is substantially transverse and parallel to the flexion-extension axis 30 of the wrist when the orthosis 1 is worn. The axis 31 can be substantially positioned at the intersection of the joining strap 16 and the distal bridge 10.

The orthosis 1 therefore allows some flexion of the wrist in direction F in FIG. 8 by an angle β possibly being in the order of 40 to 60° from the rest position illustrated in FIG. 7.

As illustrated in FIG. 8, this flexion of the wrist, and deformation of the body 2, translates as bending of the joining strap 16 which locally—typically in its central portion—is able to move away from the wrist. The cushion 19 allows comfortable flexion without any risk of compression of the dorsal muscle-ligament network of the wrist. This possibility of flexion of the wrist allows more fine-tuned grasping (pen, computer mouse, driving with change of gears, etc.) which facilitates the user's daily life.

Next, when the flexor muscles of the wrist are released, the body 2 returns to the non-stressed state by elasticity via pivoting of the distal portion 3 relative to the proximal portion 5 about the said articulation axis 31.

The joining strap 16 therefore acts as a leaf-spring which resumes shape and brings the wrist into extension. This assisted extension—in the direction of arrow E in FIG. 9—prevents repeat pulling of the epicondyle muscles on their proximal insertion. Practically no demand is placed on the inflamed tendons, which allows activity to be resumed without the risk of chronic epicondylitis.

Reference is now made to FIGS. 10 to 14 which illustrate other rigidifying means designed to prevent deformation of the body 2 of the orthosis 1 when pressure is applied to the palm support 7 opposite the joining strap 16. These rigidifying means comprise a rigid part able to be removably attached onto the joining strap 16 so as to prevent the elastic deformation of this joining strap 16. When the rigid portion is removed, the body 2 of the orthosis 1 can again deform when appropriate.

In FIG. 10 the rigid part comprises an oblong ring 35 which fastens onto a first stud 36 located substantially at the intersection between the joining strap 16 and the proximal bridge 12, and onto a second stud 37 located substantially at the intersection between the joining strap 16 and the distal bridge 10. The oblong ring 35 has some elasticity so that it can be placed in position on the studs 36, 37 whilst preventing deformation of the joining strap 16.

In FIG. 11 the rigid part comprises a ridge 38 which press fits under a first arch 39 located substantially at the intersection between the joining strap 16 and the proximal bridge 12 and underneath a second arch 40 located substantially at the intersection between the joining strap 16 and the distal bridge 10. In mounted position, the ridge 38 is located substantially in a plane (D1, D3). It has some elasticity so that it can be positioned in the arches 39, 40 whilst preventing deformation of the joining strap 16.

In FIG. 12 the rigid part comprises a strip 41 comprising a central convex portion 42 and a hook 43 at each of its ends, the hooks 43 facing away from the convex portion. The hooks hook onto a first projection 44 located substantially at the intersection between the joining strap 16 and the proximal bridge 12 and onto a second projection 45 located substantially at the intersection between the joining strap 16 and the distal bridge 10.

Starting from the rigidifying position (FIG. 13) in which the strip 41 is hooked onto the projections 44, 45 and prevents deformation of the joining strap 16, a user can press on the convex portion 42 (in the direction of the arrow in FIG. 14). As a result the ends of the strip 41 lift up, thereby freeing the hooks 43 from the projections 44, 45.

The invention is evidently not limited to the above-described embodiments given as examples, but encompasses all technical equivalents and variants of the described means and the combinations thereof.

The invention claimed is:

1. An orthosis for treating muscle disorders of an elbow, the orthosis including a body comprising:
    a distal portion arranged to be placed at a level of a hand, and including a substantially transverse palm support for a palm of the hand, and extending in a proximal direction by two substantially longitudinal lateral branches joined at their proximal end by a substantially transverse distal bridge arranged to be placed over a posterior side of a wrist;
    a proximal portion arranged to be placed at a level of a forearm and including two substantially longitudinal lateral wings arranged to bear on either side of the forearm and which are joined at their distal end by a substantially transverse proximal bridge arranged to be placed over the posterior side of the forearm;
    a back joining strap extending substantially longitudinally and connecting the substantially transverse distal bridge and substantially transverse proximal bridges;
    a strap associated with each of the substantially longitudinal lateral wings of the proximal portion to hold the lateral wings tight against each other, and passing underneath the anterior side of the forearm, the body of the orthosis having a geometry such that a relative position of the distal and proximal portions, in a non-stressed state, corresponds to holding in extension of the wrist when the orthosis is worn;
    wherein the joining strap is elastically deformable so that when pressure is applied to the palm support opposite the joining strap, the joining strap becomes deformed to allow pivoting of the distal portion relative to the proximal portion about an articulation axis which is substantially transverse and parallel to a flexion-extension axis of the wrist when the orthosis is worn;
    wherein when said pressure is released, the body returns to the non-stressed state via elasticity by pivoting of the distal portion relative to the proximal portion about said articulation axis;
    wherein the body is made in a single piece in semi-rigid material.

2. The orthosis according to claim 1, wherein said orthosis further comprises a rigidifying device arranged to prevent deformation of the body of the orthosis when pressure is applied to the palm support opposite the joining strap.

3. The orthosis according to claim 2, wherein the rigidifying device comprises a rigid part fastened onto the joining strap removable to prevent elastic deformation of the joining strap.

4. The orthosis according to claim 3, wherein the rigidifying device comprises at least one rigid member mounted on the proximal portion, respectively on the distal portion of the body of the orthosis, to pivot about a substantially transverse axis between an active position in which the member is fastened onto the distal portion, respectively onto the proximal portion, by retaining a device, to prevent deformation of the body of the orthosis, and an inactive position in which the member allows deformation of the body of the orthosis.

5. The orthosis according to claim 4, wherein the at least one rigid member comprises a lateral tab having a first end which is mounted on a lateral wing of the proximal portion, respectively a lateral branch of the distal portion, of the body of the orthosis, and a second end which is provided with removable retaining means on said lateral branch and said lateral wing, in active or inactive position.

6. The orthosis according to claim 1, wherein said orthosis further comprises a cushion attached underneath a dorsal or posterior part of the body of the orthosis, underneath at least part of the distal bridge and of the joining strap, the cushion is arranged to be inserted between the user's wrist and the body of the orthosis.

7. The orthosis according to claim 6, wherein the cushion comprises at least one raised portion extending substantially transversely and facing the hand when the orthosis is worn.

8. The orthosis according to claim 1, wherein said orthosis is free of any member bearing on the dorsal side of the hand such as a strap or equivalent.

9. The orthosis according to claim 1, wherein the transverse distal bridge comprises a notch arranged on its distal edge and located in a region of an ulnar styloid when the orthosis is worn.

10. The orthosis according to claim 1, wherein the body is transparent or translucent.

* * * * *